United States Patent
Yamashita et al.

(10) Patent No.: US 8,415,163 B2
(45) Date of Patent: Apr. 9, 2013

(54) METHOD OF DIAGNOSING RENAL DYSFUNCTION IN A CAT BASED ON NON-CAUXIN PROTEIN LEVELS

(75) Inventors: Tetsuro Yamashita, Iwate (JP); Yasuyuki Suzuta, Fukushima (JP)

(73) Assignees: Incorporated National University Iwate University, Iwate (JP); Nippon Zenyaku Kogyo Co., Ltd., Fukushima (JP)

( * ) Notice: Subject to any disclaimer, the term of this patent is extended or adjusted under 35 U.S.C. 154(b) by 0 days.

(21) Appl. No.: 13/587,255

(22) Filed: Aug. 16, 2012

(65) Prior Publication Data

US 2012/0309110 A1 Dec. 6, 2012

Related U.S. Application Data

(62) Division of application No. 12/452,687, filed as application No. PCT/JP2007/064724 on Jul. 20, 2007, now Pat. No. 8,268,639.

(51) Int. Cl.
 G01N 33/545 (2006.01)
 G01N 33/548 (2006.01)

(52) U.S. Cl.
 USPC ............... 436/86; 436/529; 436/531; 435/7.1

(58) Field of Classification Search .................. None
See application file for complete search history.

(56) References Cited

U.S. PATENT DOCUMENTS

| | | |
|---|---|---|
| 5,145,789 A | 9/1992 | Corti et al. |
| 5,558,834 A | 9/1996 | Chu et al. |
| 8,268,639 B2 | 9/2012 | Yamashita et al. |
| 2004/0115725 A1 | 6/2004 | Pieper et al. |
| 2004/0214171 A1 | 10/2004 | Yamashita et al. |
| 2006/0094863 A1 | 5/2006 | Yamashita et al. |
| 2006/0270051 A1 | 11/2006 | Jenkins et al. |

FOREIGN PATENT DOCUMENTS

JP 2003-250575 9/2003

OTHER PUBLICATIONS

Experiment Course in New Biochemistry 3 (Shin Seikagaku Jikken Koza 3), Carbohydrate I, Glycoproteins (the First Volume), pp. 3-29, Tokyo Kagaku Dojin Co., Ltd., May 21, 1990, along with a brief English language explanation thereof.

Miyazaki et al., "Species-, sex-, and age-dependent urinary excretion of cauxin, a mammalian carboxylesterase" *Comparative Biochemistry and Physiology*. Part B, vol. 145, No. 3-4, pp. 270-277, published online Aug. 25, 2006.

Miyazaki et al., "A major urinary protein of the domestic cat regulates the production of felinine, a putative pheromone precursor" *Chemistry and Biology*, vol. 13, No. 10, pp. 1071-1079, Oct. 20, 2006.

(Continued)

*Primary Examiner* — Yelena G Gakh
*Assistant Examiner* — Michelle Adams
(74) *Attorney, Agent, or Firm* — Greenblum & Bernstein, P.L.C.

(57) ABSTRACT

Disclosed is a method of diagnosing renal dysfunction in a cat by removing cauxin from cat urine and detecting a protein in the cat urine sample from which cauxin has been removed. Cauxin is removed from cat urine by bringing the cat urine into contact with a lectin or with an anti-cauxin antibody that specifically binds to cauxin. Cauxin may be removed using a column filled with a carrier that is bound to the lectin or to the anti-cauxin antibody. The lectin may be *Lens culinaris* lectin. Detection of the cat urinary protein from which cauxin has been removed is performed with a urine test strip.

10 Claims, 19 Drawing Sheets

OTHER PUBLICATIONS

Miyazaki et al., "Molecular cloning and characterization of a novel carboxylesterase-like protein that is physiologically present at high concentrations in the urine of domestic cats (*Felis catus*)" *Biochemical Journal*, vol. 370, pp. 101-110, 2003 (published as BJ Immediate Publication Oct. 25, 2002, Doi: 10.1042/BJ20021446).

Matsumoto et al., "Factors affecting struvite ($MgNH_4PO_4 \cdot 6H_2O$) crystallization in feline urine" *Biochimica et Biophysica Acta*, vol. 1780, No. 2, pp. 233-239, published online Sep. 29, 2007.

Extended European Search Report that issued with respect to European Patent Application No. 07791418.2, dated Jun. 14, 2010.

Urine Test Strip, Wikipedia website http://en.wikipedia.org/wiki/Urine_test_strip, dated Feb. 24, 2012.

Chial, H.J. et al., "A Spectral Study of the Charge Forms of Coomassie Blue G" *Analytical Biochemistry*, 1993, 209, 258-266.

Matsumoto et al., "Animation and Subsequent Derivatization of Epoxy-Activated Agarose for the Preparation of New Affinity Adsorbents" *J. Biochem.*, 1980, 87, 535-540.

Reisfeld, R.A. et al., "The Immunologic and Molecular Profiles of HLA Antigens Isolated from Urine" *Journal of Immunology*, 1977, 118, 264-269.

Miyazaki et al., "Tubulointerstitial nephritis causes decreased renal expression and urinary excretion of cauxin, a major urinary protein of the domestic cat" *Research in Veterinary Science*, vol. 82, No. 1, pp. 76-79, Feb. 2007.

Suzuki et al., "Structural characterization of N-glycans of Cauxin by MALDI-TOF Mass Spectrometry and Nano LC-ESI-Mass Spectrometry" *Biosci. Biotechnol. Biochem.*, vol. 71, No. 3, Mar. 7, 2007, pp. 811-816.

International Search Report dated Sep. 4, 2007 that issued with respect to PCT/JP2007/064724.

LCA-Sepharose

Sepharose CL-6B

Control         LCA-TOYOPEARL
① ② ③ ④ ⑤ ⑥ ⑦ ⑧ ① ② ③ ④ ⑤ ⑥ ⑦ ⑧ pre

METHOD OF DIAGNOSING RENAL DYSFUNCTION IN A CAT BASED ON NON-CAUXIN PROTEIN LEVELS

CROSS-REFERENCE TO RELATED APPLICATIONS

The present application is a divisional of U.S. application Ser. No. 12/452,687, which is a National Stage of International Patent Application No. PCT/JP2007/064724, filed Jul. 20, 2007. The disclosures of application Ser. Nos. 12/452,687 and PCT/JP2007/064724 are expressly incorporated by reference herein in their entireties.

FIELD OF THE INVENTION

The present invention relates to a urine test for cats in the veterinary clinical field, a method for diagnosing renal dysfunction in cats by detecting a cat urinary protein, and a diagnostic agent for renal dysfunction in cats.

BACKGROUND ART

As a cat kept as a pet becomes older, it becomes more subject to kidney diseases. Since the diseases occupy a higher rank of the cause of death of cats, early diagnosis for kidney diseases in cats has become an important object in the clinical settings of the veterinary clinical field for small animals. A measurement of a protein quantity excreted in urine has been used as an initial diagnosis for kidney diseases in humans. Proteinuria has been utilized as a diagnostic marker to indicate a renal abnormality at an early stage. However, in cats, physiological proteinuria (cauxin urine) and diseased proteinuria cannot be distinguished with a commercially available urine test strip because a high level of proteinaceous cauxin derived from the kidney of even healthy cats exists in the urine. A method for detecting kidney diseases in cats by measuring urinary cauxin has been reported, but the method requires a special reagent (cf. Patent Document 1). Therefore, a test strip for protein measurement generally used in the urinalysis cannot be used, and development of a simple and easy analysis method is desired. In addition, since there is a big sex difference in the content of cauxin present in the urine, it has been difficult in this respect to detect kidney diseases by the detection of cauxin.

Patent Document 1: Japanese Patent Application Laid-Open No. 2003-250575

SUMMARY OF THE INVENTION

The present invention is intended to provide a method for diagnosing kidney diseases in cats by detecting a cat urinary protein without being affected by cauxin, using a test strip for protein measurement generally used in the urinalysis, as well as to provide a diagnostic agent therefor.

Cauxin secreted in the urine of healthy cats is a glycoprotein having a molecular weight of approximately 70 kd. The present inventors analyzed the binding between a lectin which is a plant seed-derived protein that specifically binds to glycoproteins, and a cat urinary protein, and found that a lectin derived from *Lens culinaris* specifically binds to cauxin, but binds to other urinary proteins to a lesser extent. Accordingly, a gel which had been bound to lentil lectin (lentil lectin Sepharose) was added to a cat urine sample and suspended, and then analysis of proteins in the supernatant was performed. As a result, only cauxin was adsorbed on the gel, and the other urinary proteins were collected in the supernatant. Use of this method makes it possible to specifically remove only cauxin from the cat urine and easily detect the urinary protein derived from renal dysfunction. The present invention has been completed based on these findings.

In other words, aspects of the present invention are as follows.

[1] A method of detecting a cat urinary protein derived from renal dysfunction in a cat, including removing cauxin from cat urine and detecting a protein in a cat urine sample from which cauxin has been removed.

[2] The method of detecting a cat urinary protein derived from renal dysfunction in a cat according to item [1], wherein cauxin is removed from the cat urine by bringing the cat urine into contact with a lectin or an anti-cauxin antibody that specifically binds to cauxin.

[3] The method of detecting a cat urinary protein derived from renal dysfunction in a cat according to item [2], wherein cauxin is removed from the cat urine by using a carrier which is bound to a lectin or an anti-cauxin antibody that specifically binds to cauxin.

[4] The method of detecting a cat urinary protein derived from renal dysfunction in a cat according to item [3], wherein cauxin is removed from the cat urine by using a column filled with a carrier which is bound to a lectin or an anti-cauxin antibody that specifically binds to cauxin.

[5] The method of detecting a cat urinary protein derived from renal dysfunction in a cat according to any one of items [2] to [4], wherein the lectin is *Lens culinaris* lectin.

[6] The method of detecting a cat urinary protein derived from renal dysfunction in a cat according to any one of items [1] to [5], wherein the detection of the cat urinary protein from which cauxin has been removed is performed with a urine test strip for the detection of a urinary protein.

[7] The method of detecting a cat urinary protein derived from renal dysfunction in a cat according to any one of items [2] to [6], wherein the lectin that specifically binds to cauxin is *Lens culinaris* lectin.

[8] The method of detecting a cat urinary protein derived from renal dysfunction in a cat according to any one of items [3] to [7], wherein the carrier which is bound to the lectin that specifically binds to cauxin is Sepharose (registered trademark) or TOYOPEARL (registered trademark).

[9] A diagnostic method of renal dysfunction in a cat, including detecting a cat urinary protein by the detection method of a cat urinary protein according to any one of items [1] to [8] and deciding whether or not the cat suffers from renal dysfunction.

[10] A detection reagent for a urinary protein derived from renal dysfunction in a cat, including a carrier which is bound to a lectin or an anti-cauxin antibody that specifically binds to cauxin, and a urine test strip for the detection of a urinary protein.

[11] The detection reagent for a urinary protein derived from renal dysfunction in a cat according to item [10], including a column filled with a carrier which is bound to a lectin or an anti-cauxin antibody that specifically binds to cauxin, and a urine test strip for the detection of a urinary protein.

[12] The detection reagent for a urinary protein derived from renal dysfunction in a cat according to item [10] or [11], wherein the lectin that specifically binds to cauxin is *Lens culinaris* lectin.

[13] The detection reagent for a urinary protein derived from renal dysfunction in a cat according to any one of items [10] to [12], wherein the carrier which is bound to the lectin that specifically binds to cauxin is Sepharose (registered trademark) or TOYOPEARL (registered trademark).

[14] A diagnostic agent for renal dysfunction in a cat, including the detection reagent for a urinary protein derived from renal dysfunction in a cat according to any one of items [11] to [13].

BRIEF DESCRIPTIONS OF THE DRAWINGS

BEST MODES FOR CARRYING OUT THE INVENTION

Figure 1:
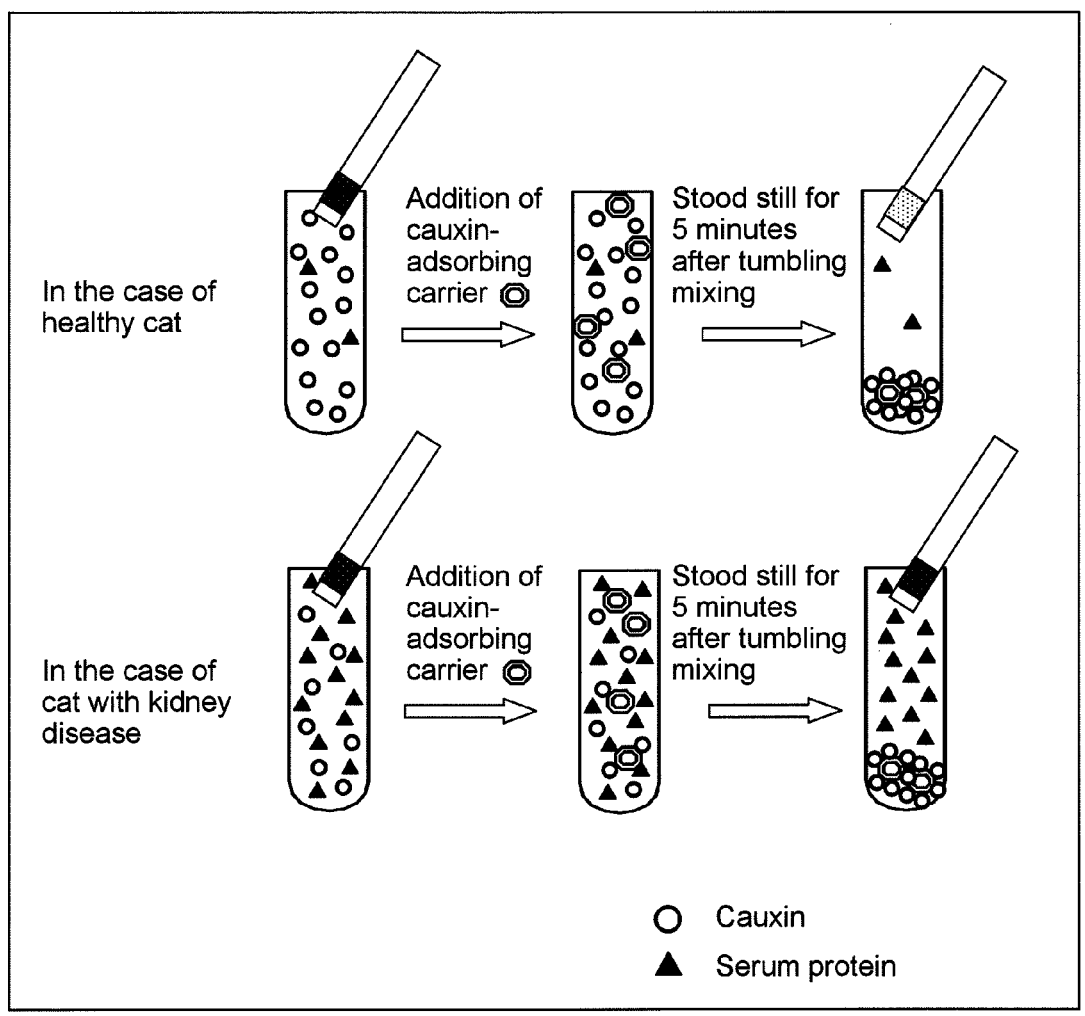
FIG. 1 is a schematic diagram showing a diagnostic kit for a urinary protein of cats.

In the method of the present invention, renal dysfunction in cats is diagnosed by removing cauxin from cat urine and measuring proteins that remaining in the cat urine.

The cat in the present invention means an animal belonging to the family Felidae and examples there of include animals belonging to the subfamily Felidae, such as *Felis catus* (domestic cat), *Puma concolor* (puma), and *Felis silvestris* (wild cat), animals belonging to the subfamily Pantherinae, such as leopard, lion, tiger, and jaguar, and animals belonging to the subfamily Acinonychinae, such as cheetah.

Removal of cauxin from cat urine can be performed using a substance that specifically binds to cauxin. Here, the substance that specifically binds to cauxin means a substance that specifically binds to cauxin present in cat urine, but does not bind to a protein other than cauxin present in cat urine, particularly a protein present in the urine at a high concentration in the case where the cat suffers from renal dysfunction. Examples of the protein other than cauxin present in the cat urine include albumin, globulin, $\beta$2-microglobulin, and the like. Examples of the substance that specifically binds to cauxin include a lectin, an anti-cauxin antibody, and the like. Examples of the lectin that specifically binds to cauxin include concanavalin A (Con A), *Lens culinaris* (lentil) lectin (LCA), *Arachis hypogaea* (peanut) lectin (PNA), *Ricinus communis* (castor bean) lectin (RCA), *Phaseolus vulgaris* (kidney bean or common bean) lectin, *Triticum vulgare* (wheat germ) lectin (WGA), *Pisum sativum* (pea) lectin (PSA), *Vicia faba* (broad bean) lectin (VFA), and the like. Among them, *Lens culinaris* lectin (LCA) having a high binding affinity to cauxin is preferable. Moreover, compounds that specifically bind to cauxin, such as substrates for cauxin and analogs thereof, can be mentioned.

An anti-cauxin antibody is easily available as a polyclonal or monoclonal antibody by purifying cauxin from cat urine and immunizing an animal with it.

Removal of cauxin may be performed by bringing cat urine into contact with a substance that specifically binds to cauxin and removing the resulting complex of cauxin with the substance that specifically binds to cauxin. For example, cat urine from which cauxin has been removed can be obtained by allowing a substance that specifically binds to cauxin to bind to a suitable carrier, packing the bound carrier into a column, passing cat urine through the column, and collecting the passed urine. In addition, the complex of the carrier with cauxin may be removed by adding, to cat urine, a carrier to which a substance that specifically binds to cauxin is bound, and performing a reaction for a fixed time, followed by centrifugation or filtration. Furthermore, the complex of cauxin with a substance that specifically binds to cauxin may be removed by adding, to urine, a substance in a free state that specifically binds to cauxin, and performing a reaction for a fixed time, followed by centrifugation. As the carrier for binding the substance that specifically binds to cauxin, celluloses, such as Sepharose (registered trademark), Sephadex (registered trademark), Cellulofine (registered trademark), and TOYOPEARL (registered trademark) for affinity chromatography (AFC type), and resins, such as agarose, dextran, silica, a vinyl polymer, and a synthetic polymer can be used, and the substance and cauxin can be bound together by a known method. For example, TOYOPEARL AF-Tresyl-650, TOYOPEARL AF-Carboxy-650, TOYOPEARL AF-Formyl-650, TOYOPEARL AF-Amino-650, and TOYOPEARL AF-Epoxy-650 (Tosoh Corporation) can be used. In addition, carriers to which various lectins are bound are commercially available, and these commercially available lectin-bound carriers may be used. Examples of the commercially available carrier include LCA-Sepharose (Amersham plc), *Lens culinaris* lectin-agarose (Seikagaku Corporation), and the like. The method for separating a protein that binds to a lectin by utilization of a lectin is known as affinity chromatography using a lectin column, and determination of lectins to be used, binding between a lectin and a carrier, preparation of a column, and determination of binding conditions between a lectin column and proteins, and the like, can be performed according to the description, for example, in "Experiment Courses in New Biochemistry 3 (Shin Seikagaku Jikken Koza 3), Carbohydrate I, Glycoproteins (the First Volume), pages 3 to 29, TOKYO KAGAKU DOJIN CO., LTD, published on May 21, 1990."

Moreover, when a column containing a carrier to which a substance that specifically binds to cauxin is bound is used, a minicolumn is preferably used so that the detection of the urinary protein is possible even if a small amount of cat urine is used. The capacity of the minicolumn is 100 µL to 2000 µL, for example. For example, cat urine from which cauxin has been removed can be obtained by stuffing absorbent cotton, filter paper, or the like on the apex of a commercially available tip (blue tip or yellow tip) for micropipettes made of a resin such as polypropylene, further stuffing a carrier to which a substance that specifically binds to cauxin is bound, thereby to prepare a minicolumn for the removal of cauxin, adding the cat urine to the minicolumn, and collecting the urine which has passed through the column. In this case, a buffer such as a Tris buffer or a phosphate buffer may be used for the equilibration of the column and for the passage of the protein adsorbed on the column.

On this occasion, the quantitative rate of the substance that specifically binds to cat urine and cauxin is not limited, and the substance may be brought into contact with the cat urine at a quantitative rate being able to remove all the cauxin in the cat urine. Cauxin exists in about 0.9 mg/mL in healthy cat urine, and in about 0.1 mg/mL or less in the urine of a cat suffering from renal dysfunction. In the present invention, a treatment for the removal of cauxin is carried out so that 90% or more, and preferably 95% or more of cauxin present in healthy cat urine is removed.

In order to detect renal dysfunction in a cat, proteins present in the cat urine from which cauxin has been removed may be measured. Examples of the protein able to serve as a marker of renal dysfunction include albumin, lysozyme, and haptoglobin.

The measurement of a urinary protein can be performed using a test strip for urinary protein measurement.

As such a test strip for urinary protein measurement, any known commercially available one may be used. Examples of the commercially available test strip include PRETEST manufactured by Wako Pure Chemical Industries Ltd. The test strip is a test strip which is soaked with a pH indicator such as bromophenol blue or tetrabromophenol blue and a pH buffer solution such as a citrate buffer solution, and detects proteins based on a protein error of the pH indicator.

In addition, such detection of proteins can be performed by the Bradford method, the BCA protein assay, the sulfosalicylic acid method, and the like.

In the case of a cat, it is possible to diagnose whether or not the cat suffers from renal dysfunction by the protein concentration in the urine from which cauxin has been removed. If the protein concentration in the cat urine is about 100 to several hundred µg/mL preferably about 100 to about 200 µg/mL or more, it is very likely that the cat suffers from renal dysfunction. Whether or not the cat suffers from renal dysfunction is finally diagnosed by the general judgment of a veterinarian.

According to the method of the present invention, the protein in the cat urine derived from renal dysfunction can be detected and renal dysfunction in a cat can be diagnosed.

Further, the present invention includes a carrier which is bound to a substance that specifically binds to cauxin or a column filled with the carrier, as well as a reagent or a kit for the detection of a cat urinary protein derived from renal dysfunction including a test strip for the detection of a urinary protein. In addition, the present invention includes a diagnostic agent or a diagnostic kit for renal dysfunction in cats, including the reagent.

Hereinafter, the present invention will be specifically explained by referring to the following examples, but the scope of the present invention should not be limited thereto.

Example 1

Figure 2:
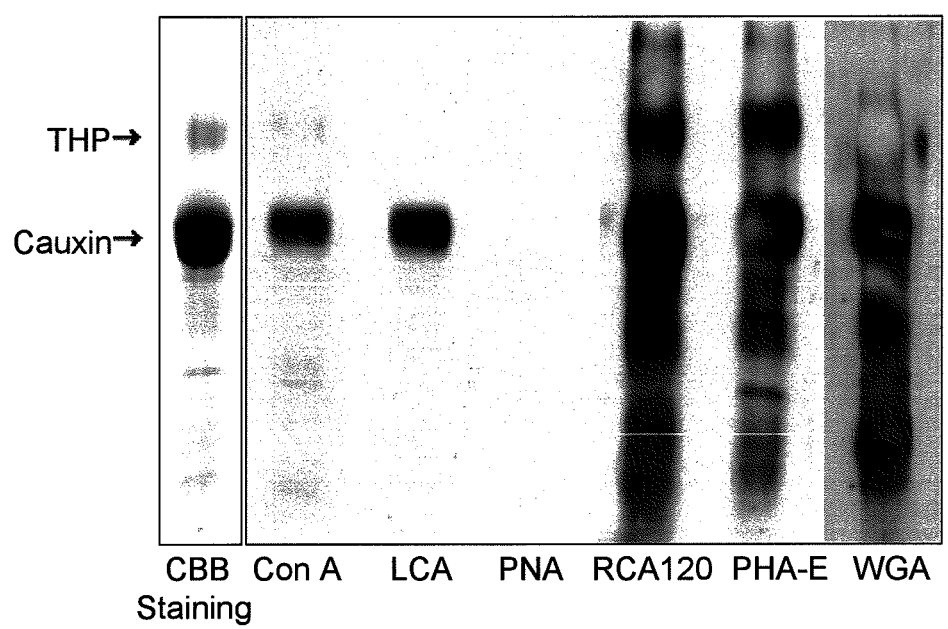
FIG. 2 is a diagram showing a reaction of various lectins with cauxin by a lectin blot analysis.

A lectin is a protein having an activity to recognize a sugar chain of a glycoprotein and specifically bind to it. As a result of studies on the binding activity of various lectins to the sugar chain of cauxin, it became clear that *Lens culinaris* lectin (hereinafter abbreviated as LCA) showed a high affinity to urinary cauxin and was specifically bound to the urinary cauxin (FIG. 2).

Figure 3:
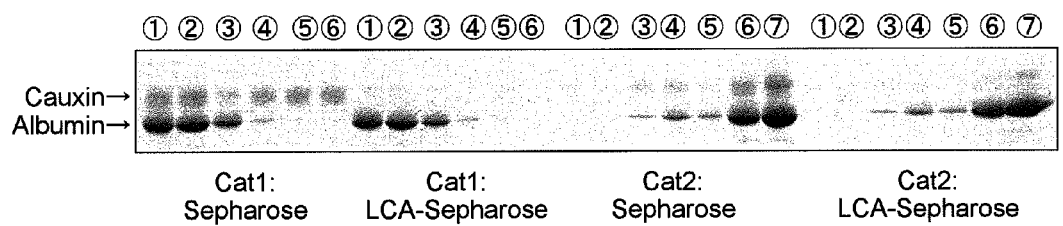
FIG. 3 is a diagram showing the results of the removal of cauxin from a urine sample by LCA-cauxin.

An experiment for removing urinary cauxin was performed by adding cat urine to LCA-Sepharose (Amersham) which is an affinity carrier bound to LCA. A urine sample (50 µL) was added to 100 µL of LCA-Sepharose, the mixture was tumbled and mixed, allowed to stand on ice for 5 minutes, and centrifuged to collect a supernatant. Using as a control a Sepharose carrier which was not bound to LCA, a similar experiment was carried out. Each sample was subjected to SDS-PAGE under non-reductive conditions and CBB staining was performed to detect proteins (FIG. 3).

As a result, it was revealed that the amount of the urinary protein (albumin) except cauxin hardly changed, but cauxin was specifically adsorbed on the LCA-Sepharose carrier and was removed from the sample.

Example 2

Reaction of Lectin Carrier with Urine Utilizing Blue Tip for Micropipettes

Figure 4:
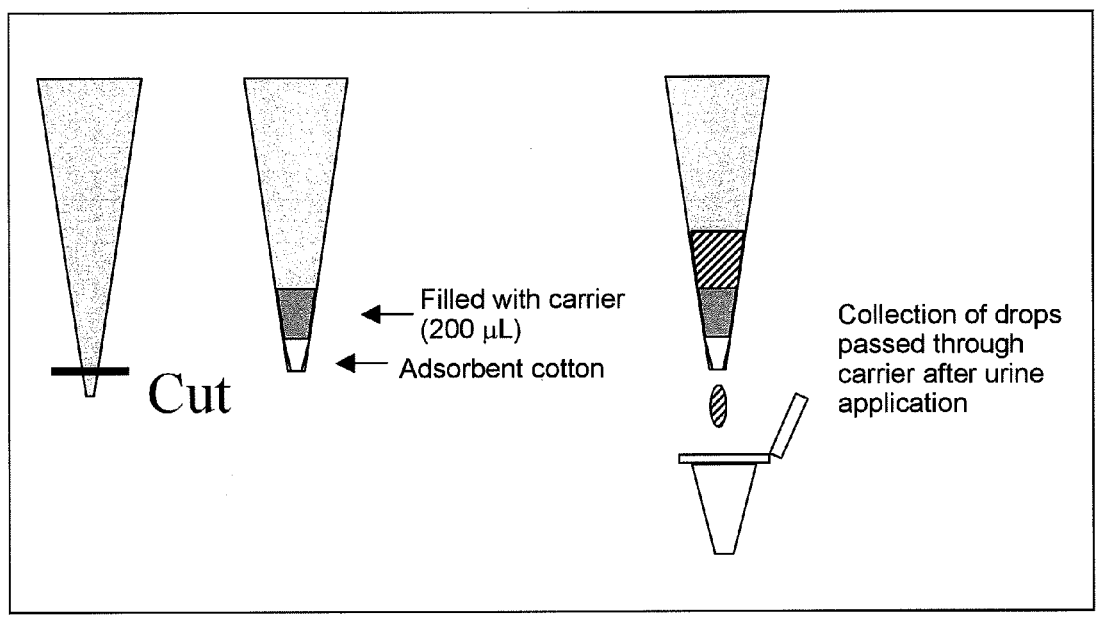
FIG. 4 is a diagram showing a production method and a use method of a carrier column utilizing a blue chip.
Figure 5:
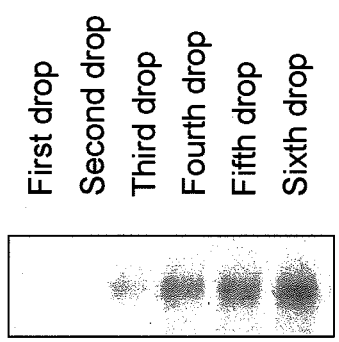
FIG. 5 is a diagram showing the results of SDS-PAGE of a urine sample which has been passed through a carrier column.
Figure 5:
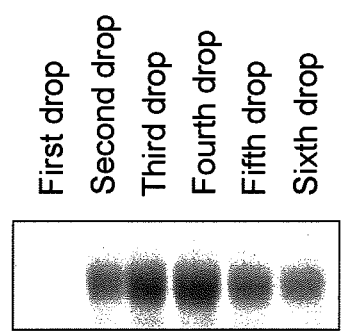
Figure 6A:
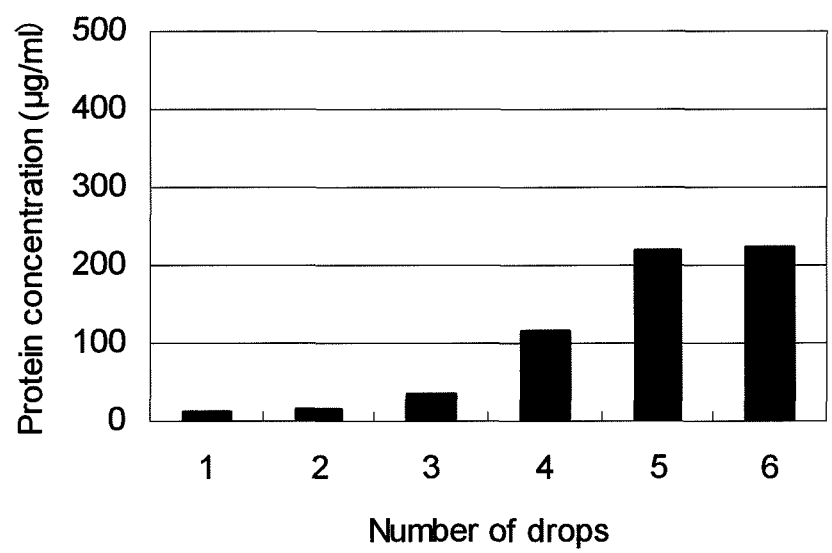
FIG. 6A is a graph showing the amount of proteins in a urine sample which has been passed through a carrier column (LCA-Sepharose column).
Figure 6B:
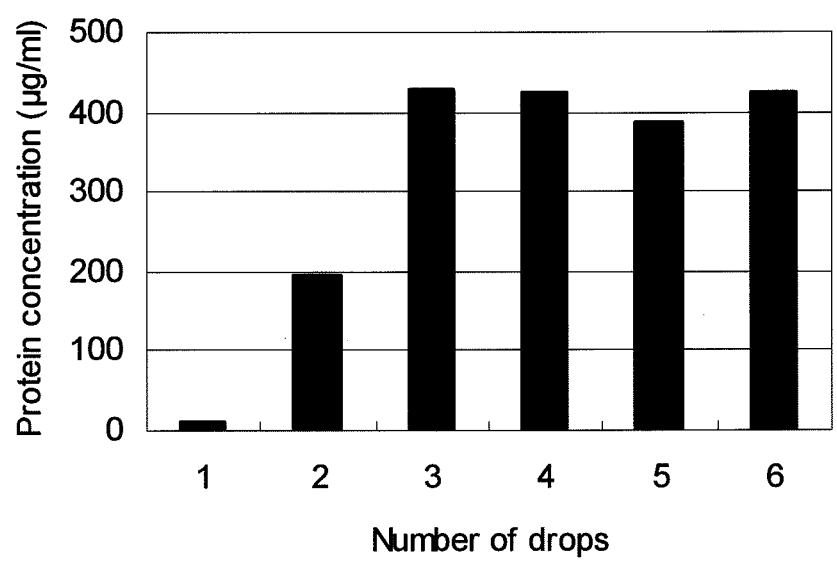
FIG. 6B is a graph showing the amount of proteins in a urine sample which has been passed through a Sepharose CL-6B column used as a control.

As shown in FIG. 4, a blue tip was filled with 200 µL of LCA-Sepharose and equilibrated with TBS, and 300 µL of urine was applied thereto to pass through the column, and drops of the passed urine was collected (one drop: about 50 µL). The collected urine (10 µL) was applied to SDS-PAGE under non-reductive conditions and the gel was stained with CBB (FIG. 5), and then proteins were quantified by the Bradford method (FIG. 6).

In the control, the equilibrated buffer was all replaced by the urine at the stage of the third to fourth drops. It was elucidated that, on the tip stuffed with 200 µL of LCA Sepharose, 90% or more of proteins were adsorbed in the third drop fraction. It is believed that it becomes possible to obtain a fraction from which cauxin is almost wholly removed by adding urine to such a minicolumn, and collecting a sample after application of several drops of the urine.

Example 3

Removal of Cauxin by Using TOYOPEARL Carrier

Figure 7:
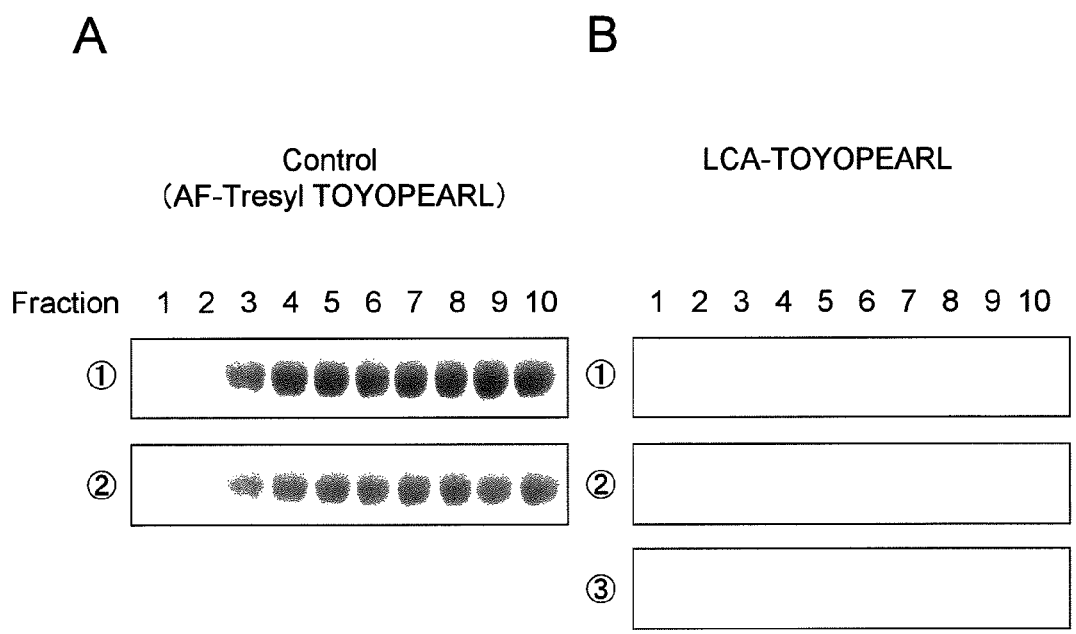
FIG. 7 is a diagram showing the results of SDS-PAGE of a urine sample from which cauxin has been removed using a TOYOPEARL carrier.
Figure 8A:
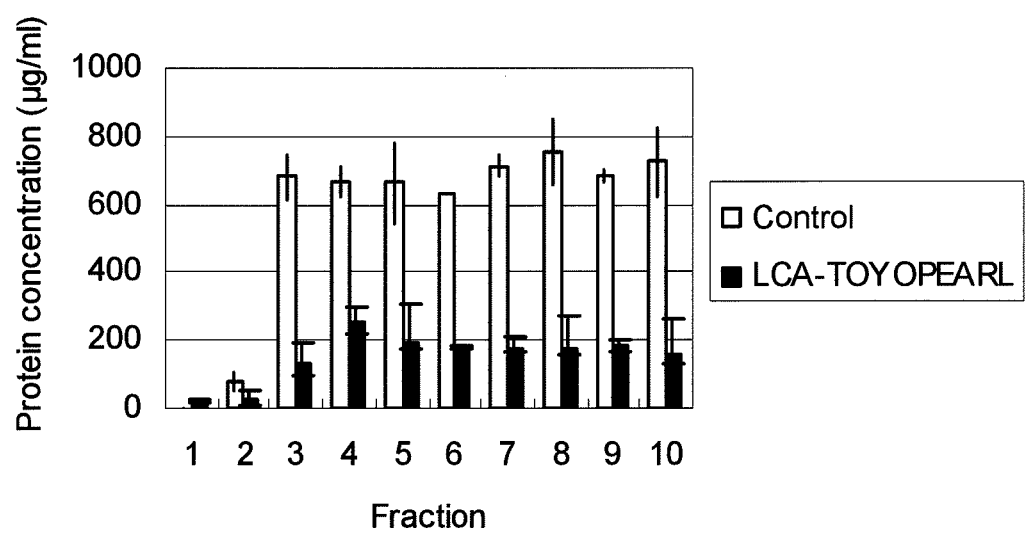
FIG. 8A is a graph showing the results of the quantification of the amount of cauxin by the Bradford quantification method using an SDS-PAGE gel of a urine sample from which cauxin has been removed using a TOYOPEARL carrier.
Figure 8B:
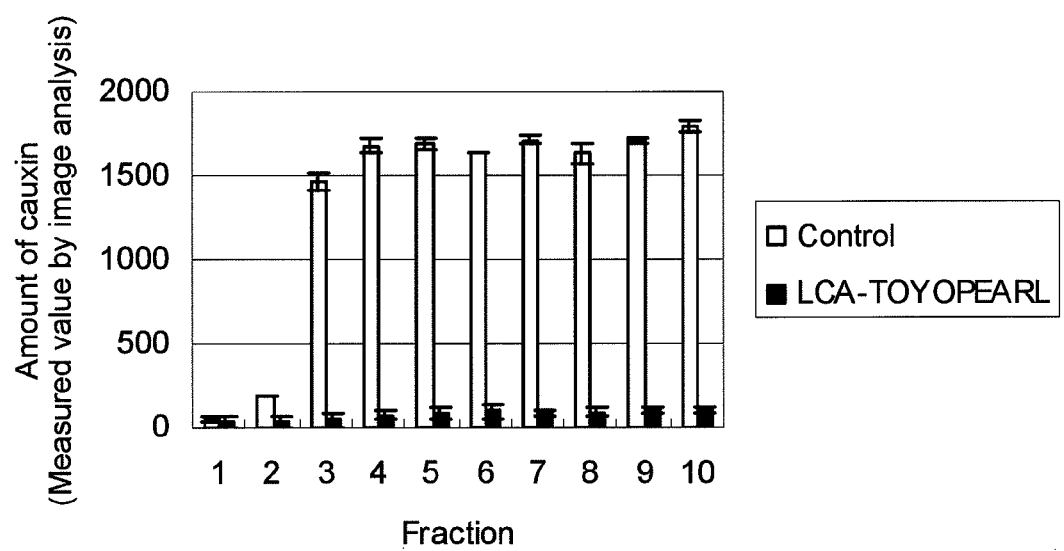
FIG. 8B is a graph showing the results of the quantification of the amount of cauxin by densitometric quantification using an SDS-PAGE gel of a urine sample from which cauxin has been removed using a TOYOPEARL carrier.

An experiment similar to Example 2 was performed using TOYOPEARL AF-Tresyl 650M (TOHSOH, hereinafter abbreviated as TOYOPEARL) as an affinity carrier capable of binding to LCA. TOYOPEARL was weighed in an amount of 0.1 g (about 400 µL), and LCA which had been dissolved in a 0.1 M sodium phosphate buffer (pH 7.4, 2 mL) was added thereto so as to attain a ratio of 15 mg/mL (carrier), and a reaction was performed overnight by tumbling mixing at 4° C. Thereafter, the carrier was washed with 5-fold amount of 1 M NaCl, and blocking was performed with 0.1 M Tris-HCl+ 0.5 M NaCl at room temperature for 1 hour. The collected urine sample was subjected to SDS-PAGE, and a band of cauxin was quantified from an image of the gel stained with CBB (FIG. 7), using an image analysis program (BIO-RAD, Molecular Analyst) (FIGS. 8A and 8B). FIG. 8A shows the results obtained by the Bradford quantification method, and FIG. 8B shows the results obtained by the densitometric quantification method. As a result, compared to the control carrier (only a blocking treatment was performed without addition of LCA), a urine sample of the second to eighth drops from which 90 to 95% of cauxin had been removed was obtained. When the total protein concentration of the urine after being passed through the carrier was measured by a dye-binding method (BIO-RAD Quick Start Bradford Dye Reagent), the protein concentration was reduced to 25 to 30% of that before column passage. By this operation, a two stage change is observed in the judgment of a general urine test strip (PRETEST: Wako Pure Chemical Industries, Ltd.). From this result, a technique using an LCA column is considered to be effective for removing cauxin in cat urine.

A similar experiment was carried out twice. In the second experiment, 5 mm at the apex of a blue tip was cut, and the above-mentioned carrier (200 µL) was filled into the blue tip whose apex had been stuffed with absorbent cotton and then equilibrated with TBS (Tris-Buffered Saline). Urine (500 µL) was applied to this column, and eight fractions of two drops each (about 60 µL) were collected from the urine which had passed the column. Protein quantification of each of the collected fractions was performed by the Bradford method, and 10 µL of the fraction were applied to SDS-PAGE (12% acrylamide gel) under non-reductive conditions, and then the gel was stained with CBB. After destaining, a band of cauxin was quantified by densitometry. A carrier wherein the reactive group was blocked with 0.2 M Tris-HCl (pH 7.4) without addition of a lectin was filled into the same tip in the same amount, and this was used as a control.

Figure 9:
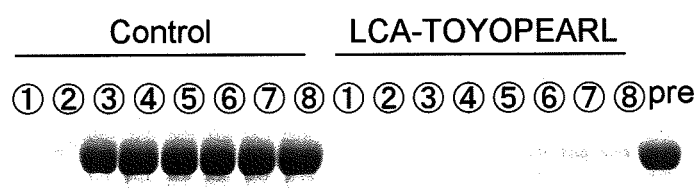
FIG. 9 is a diagram showing the results of SDS-PAGE of a urine sample from which cauxin has been removed using a cross-linked TOTOPEARL carrier.
Figure 10A:
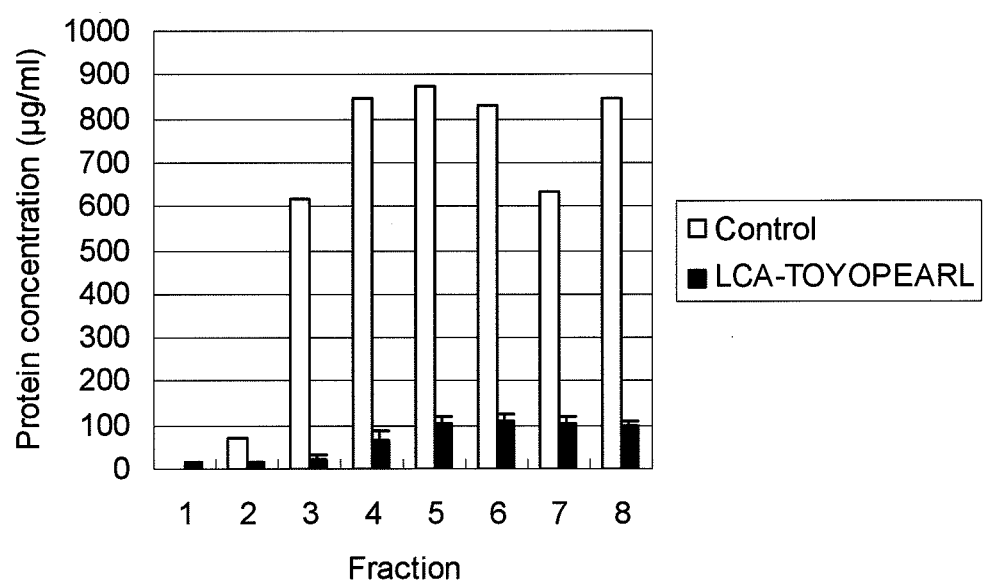
FIG. 10A is a graph showing the results of the quantification of the amount of cauxin by the Bradford quantification method using an SDS-PAGE gel of a urine sample from which cauxin has been removed using a cross-linked TOYOPEARL carrier.
Figure 10B:
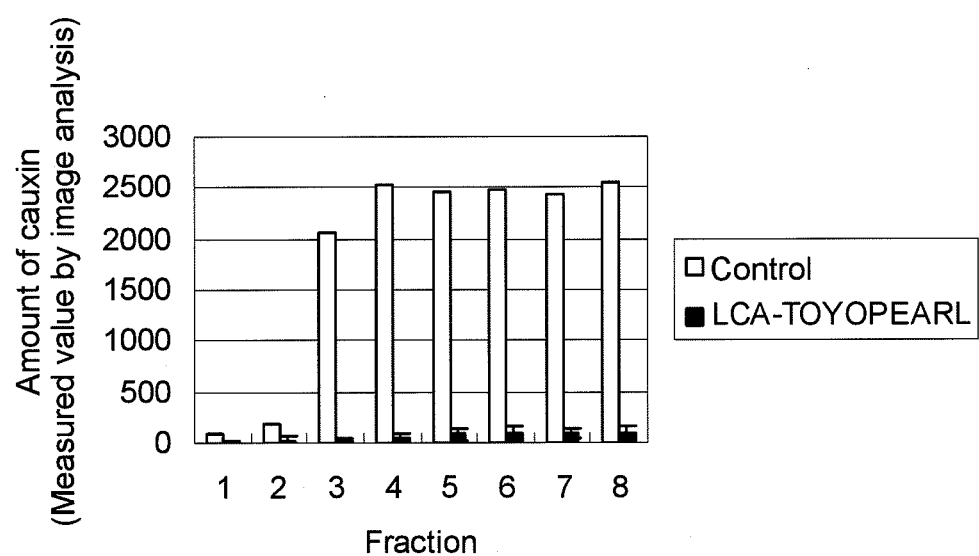
FIG. 10B is a graph showing the results of the quantification of the amount of cauxin by densitometric quantification using an SDS-PAGE gel of a urine sample from which cauxin has been removed using a cross-linked TOYOPEARL carrier.

FIG. 9 shows the results of SDS-PAGE; FIG. 10A shows the results of the Bradford assay; and FIG. 10B shows the results of the quantification using densitometry. In the protein quantification by the Bradford method, about 88% of total proteins in the fifth fraction wherein TBS had been all replaced by urine was adsorbed on the carrier, and, in the quantification of a band of cauxin by densitometry, about 96% of cauxin was adsorbed on the carrier. Thus, it was confirmed that cauxin can be removed from cat urine.

Using a urine sample from which cauxin had been removed by the method mentioned above and a urine sample from which cauxin had not been removed, a urinary protein was measured using a urine test strip (PRETEST: Wako Pure Chemical Industries, Ltd.). The results are shown in FIG. 11.

Figure 11:
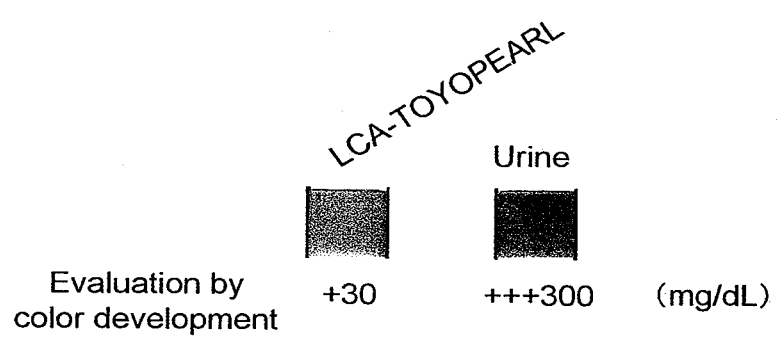
FIG. 11 is a diagram showing the results of the measurement of the amount of urinary proteins in a urine sample which has been subjected to a treatment for the removal of cauxin and a urine sample which has not been subjected to a treatment for the removal of cauxin, using a urine test strip (PRETEST, Wako Pure Chemical Industries, Ltd.).

As shown in FIG. 11, the degree of the color development was decreased in the urine sample from which cauxin had been removed.

When a similar study was performed by using TOYOPEARL AF-Formyl 650M instead of the above-mentioned TOYOPEARL AF-Tresyl 650M, similar results were obtained.

Example 4

Influences of Serum Protein

Figure 12:
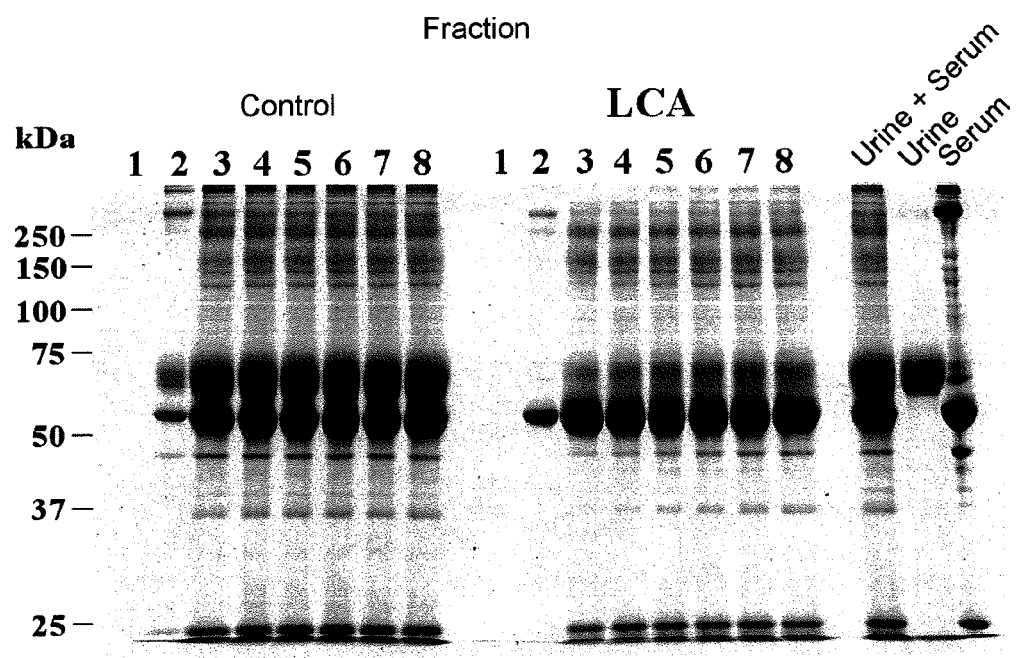
FIG. 12 is a photograph showing the results of SDA-PAGE of the urine obtained by adding, to a cross-linked TOYOPE-ARL carrier, cat urine to which serum has been added, and passing the urine through the carrier.
Figure 13:
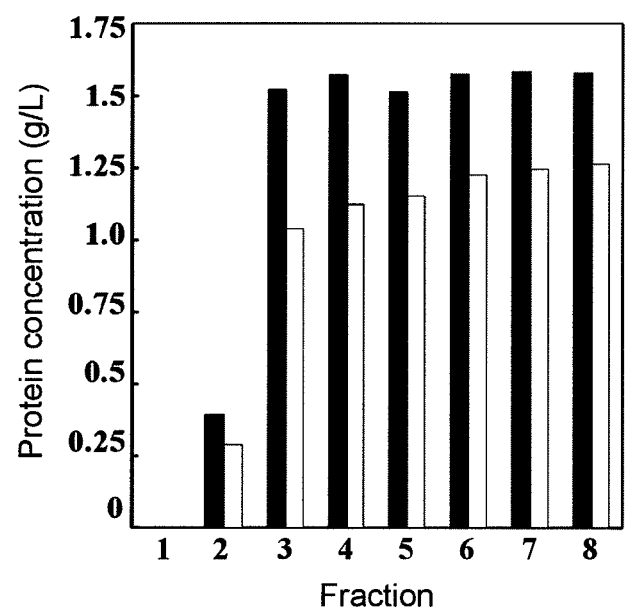
FIG. 13 is a graph showing the results of the quantification by the Bradford method of the urine obtained by adding, to a cross-linked TOYOPEARL carrier, cat urine to which serum has been added, and passing the urine through the carrier.

Using the column prepared in Example 3, influences of serum protein in the removal of cauxin were analyzed. Cat serum (10 µL) was added to 490 µL of healthy male cat urine, and the mixture was added to a carrier column, and the urinary protein which had passed the column was analyzed by the method mentioned above. FIG. 12 shows the results of SDS-PAGE of each fraction, and FIG. 13 shows the protein concentration of each fraction as measured by the Bradford method. As shown in the drawings, it was proved that only cauxin is selectively adsorbed on the column even if a high level of a serum protein exists.

Example 5

Measurement Using Urine of Cat Suffering from Renal Dysfunction

Figure 14:
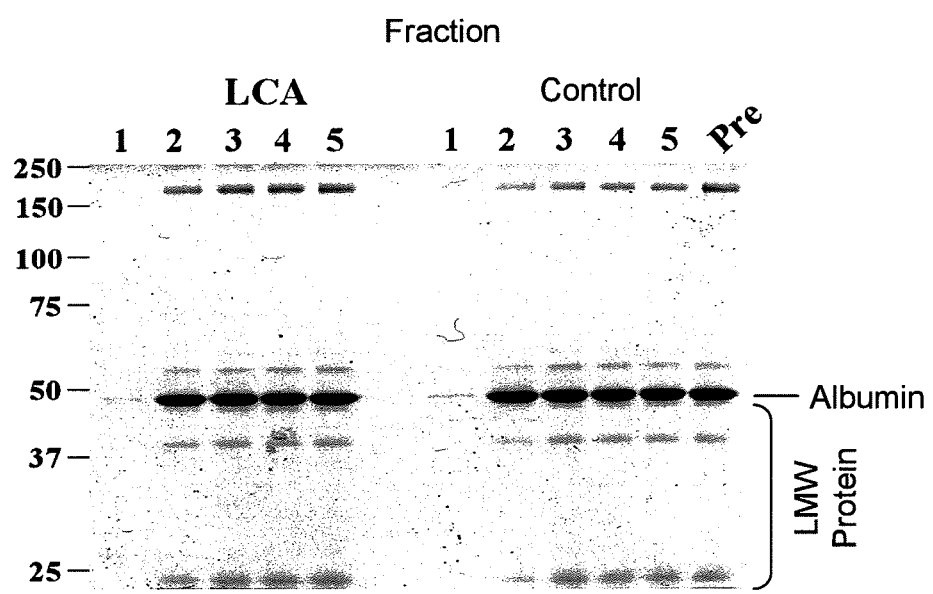
FIG. 14 is a photograph showing the results of SDS-PAGE of the urine obtained by adding, to a cross-linked TOYOPE-ARL carrier, urine of a cat suffering from a kidney disease, and passing the urine through the carrier.
Figure 15:
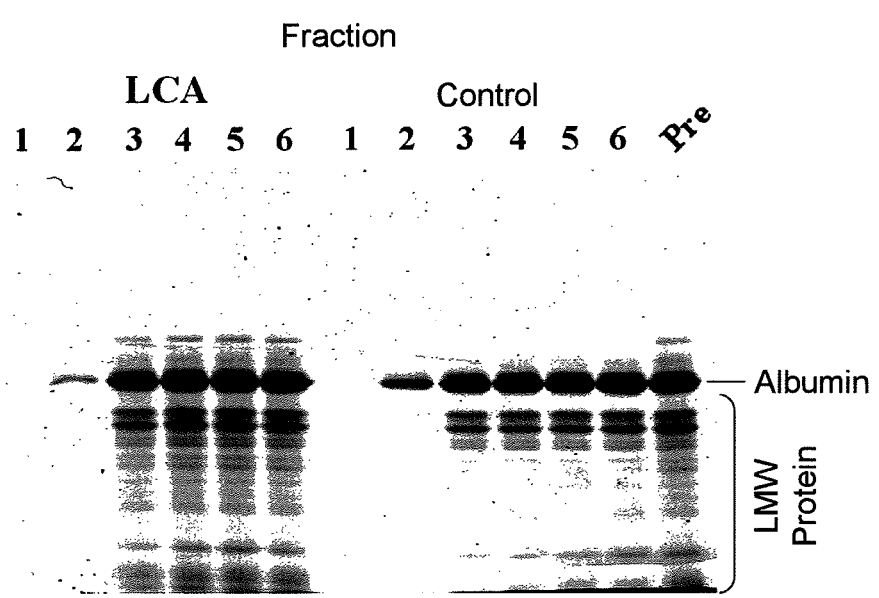
FIG. 15 is a photograph showing the results of SDS-PAGE of the urine obtained by adding, to a cross-linked TOYOPE-ARL carrier, urine of a cat suffering from a kidney disease, and passing the urine through the carrier.
Figure 16:
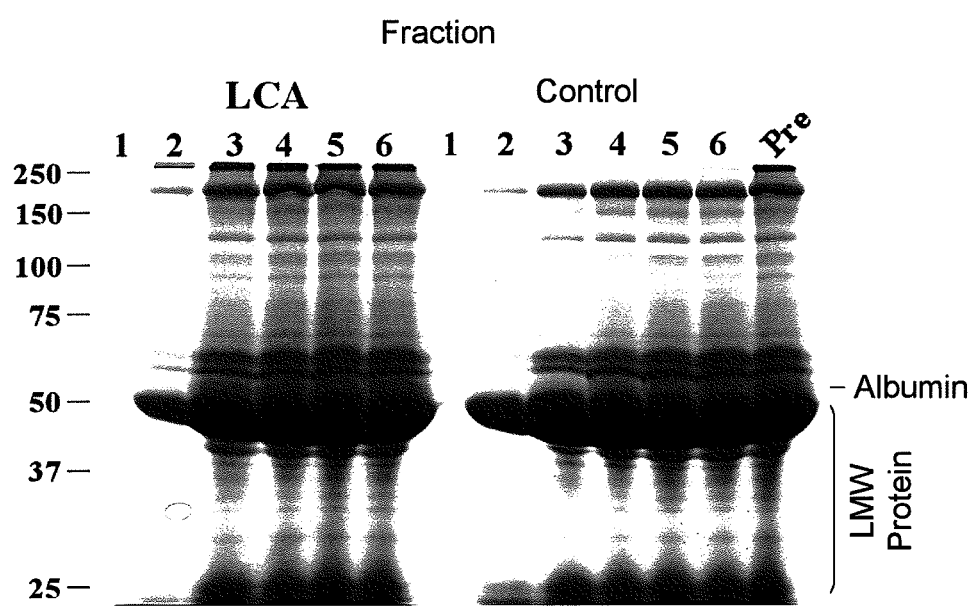
FIG. 16 is a photograph showing the results of SDS-PAGE of the urine obtained by adding, to a cross-linked TOYOPE-ARL carrier, urine of a cat suffering from a kidney disease, and passing the urine through the carrier.

An experiment similar to Examples 3 and 4 was performed using 500 µL of urine, in which almost no cauxin was found, of three cats with a kidney disease, and an elution pattern of proteins was compared to that of the control by SDS-PAGE of each fraction of the fifth to sixth fractions. The results of SDS-PAGE of each cat urine are shown in FIGS. 14 to 16. As shown in the drawings, in three cat urine samples, the patterns of the urinary protein were different from each other, but it was understood that almost no binding of proteins other than cauxin found in cats with a kidney disease to the LCA column is found.

INDUSTRIAL APPLICABILITY

In the urinalysis for cats using a protein test strip used in usual urinalyses, it is difficult to make a distinction between cauxin present in healthy urine in large quantities and a urinary protein derived from kidney diseases (renal dysfunction), but a measurement using the present technique makes it possible to selectively detect the latter protein only.

All publications, patents, and patent applications cited in this application are intended to be incorporated herein by reference in their entireties.

What is claimed is:

1. A method of determining whether a cat has renal dysfunction, the method comprising
   removing cauxin from a urine sample from the cat;
   measuring a level of protein in the urine sample from which cauxin has been removed; and
   determining whether or not the cat has renal dysfunction using the measured level of protein.

2. The method according to claim 1, wherein cauxin is removed from the urine sample by bringing the urine sample into contact with a lectin that specifically binds to cauxin or an anti-cauxin antibody that specifically binds to cauxin.

3. The method according to claim 2, wherein the lectin that specifically binds to cauxin is Lens culinaris lectin.

4. The method according to claim 1, wherein cauxin is removed from the urine sample by using a carrier, the carrier being bound to a lectin that specifically binds to cauxin or the carrier being bound to an anti-cauxin antibody that specifically binds to cauxin.

5. The method according to claim 4, wherein the lectin that specifically binds to cauxin is Lens culinaris lectin.

6. The method according to claim 4, wherein the carrier comprises agarose or vinyl polymer.

7. The method according to claim 4, wherein cauxin is removed from the urine sample by using a column filled with the carrier.

8. The method according to claim 7, wherein the lectin that specifically binds to cauxin is Lens culinaris lectin.

9. The method according to claim 7, wherein the carrier comprises agarose or vinyl polymer.

10. The method of according to claim 2, wherein the level of protein is measured using a urine test strip.

* * * * *